United States Patent [19]
Joo et al.

[11] Patent Number: 6,137,010
[45] Date of Patent: Oct. 24, 2000

[54] METHOD FOR PREPARING 4-NITRODIPHENYLAMINE AND 4-NITROSODIPHENYLAMINE FROM CARBANILIDE

[75] Inventors: Young J. Joo; Jin Eok Kim; Jeong Im Won; Kum Ui Hwang, all of Taejon, Rep. of Korea

[73] Assignee: Korea Kumho Petrochemical Co., Ltd., Rep. of Korea

[21] Appl. No.: 09/501,686

[22] Filed: Feb. 10, 2000

[30] Foreign Application Priority Data

Aug. 19, 1999 [KR] Rep. of Korea ............ 99-34301

[51] Int. Cl.[7] .................................................. C07C 207/58

[52] U.S. Cl. .................... 564/406; 564/395; 564/407

[58] Field of Search ..................... 564/406, 407, 564/395

[56] References Cited

U.S. PATENT DOCUMENTS

| | | |
|---|---|---|
| 5,117,063 | 5/1992 | Stern et al. . |
| 5,453,541 | 9/1995 | Stern et al. . |
| 5,608,111 | 3/1997 | Stern et al. . |
| 5,623,088 | 4/1997 | Stern et al. . |
| 5,684,203 | 11/1997 | Jautelat ................... 564/406 |

OTHER PUBLICATIONS

Stern et al., "Animation of Nitrobenzene via Nucleophilic Aromatic Substitution for Hydrogen: Direct Formulation of Aromatic Amide Bonds", *J. Org. Chem*, 1993, 58, 68883–6888.

Ayyangar et al., "A Novel Reaction of Acetanilide With Nitrobenzene In DMSO—An Unusual Solvent Assisted Regioselective Aromatic Nucleophilic Substitution", *Tetrahedron Letters*, vol. 31, No. 22, p. 3217–3220 (1990).

Ayyangar et al., "A Novel Synthesis Of Unsymmetrical Azo Aromatics Inaccessible By Diazo–Coupling Reaction", *Tetrahedron Letters*, vol. 30, No. 51, p. 7253–7256 (1989).

Stern et al., "Direct Coupling of Aniline and Nitrobenzene: A New Example of Nucleophillic Aromatic Substitution for Hydrogen", *J. Am. Chem. Soc.*, 1992, 114, 9237–9238.

*Primary Examiner*—Samuel Barts
*Attorney, Agent, or Firm*—Cook, Alex, McFarron, Manzo, Cummings & Mehler Ltd.

[57] ABSTRACT

This invention relates to a process for preparing 4-nitrodiphenylamine and 4-nitrosodiphenylamine to be used for 4-aminodiphenylamine as an intermediate of antiozonant, wherein carbanilide is reacted with nitrobenzene in the presence of an appropriate base, while simultaneously adding aniline to the mixture so as to regenerate some amounts of carbanilide as a starting material.

According to this invention, 4-nitrodiphenylamine and 4-nitrosodiphenylamine can be prepared in a higher selectivity and conversion rate via a continuous reaction by recycling carbanilide, a starting material, while adding a certain amount of aniline during the process. Further, the amount of waste water can be significantly reduced compared to the conventional method without any corrosive materials harmful to the environment.

13 Claims, No Drawings

METHOD FOR PREPARING 4-NITRODIPHENYLAMINE AND 4-NITROSODIPHENYLAMINE FROM CARBANILIDE

FIELD OF THE INVENTION

This invention relates to a process for preparing 4-nitrodiphenylamine and 4-nitrosodiphenylamine from carbanilide and more particularly, to the process for preparing 4-nitrodiphenylamine (hereinafter referred to as "4-NDPA") and 4-nitrosodiphenylamine (hereinafter referred to as "4-NODPA") in a very high selectivity and better yield, wherein carbanilide is reacted in nitrobenzene in the presence of an appropriate base such as sodium hydroxide and polar organic solvents, while adding aniline to the mixture simultaneously so as to regenerate some amounts of carbanilide as a starting material. Hence, 4-NDPA and 4-NODPA are generally hydrogenated and used for the manufacture of 4-aminodiphenylamine (hereinafter referred to as "4-ADPA"), an intermediate of antiozonant.

DESCRIPTION OF THE RELATED ART

The currently commercialized process for preparing 4-ADPA is largely divided into two processes; 1) the Monsanto process and 2) the Ouchi process.

According to the Monsanto process, p-chloronitrobenzene is formed by nitrating chlorobenzene, following by a reaction with formanilide to prepare 4-NDPA. Then 4-ADPA is finally prepared under the general hydrogenation. However, this process has some recognized disadvantages in that during the reaction, corrosive waste water containing chlorine needs to be properly treated, together with a large amount of organic and inorganic waste solution.

According to the Ouchi process, N-nitrosodiphenylamine is formed via reaction between diphenylamine and sodium nitrate (NaNO$_2$), followed by Fischer-Hepp rearrangement to neutralize the reactant. Then it is finally prepared under the general hydrogenation. However, this process also has some disadvantages in that a large amount of harmful waste solution is generated due to nitrosation.

In addition, other processes for preparing 4-ADPA have been disclosed via a head-tail combination reaction of aniline (U.S. Pat. No. 4,760,186) and hydrogenation of p-nitrosodiphenylhydroxylamine. However, these processes have proven to be uneconomical for commercialization including having a low yield.

In recent years, a process involving nucleophilic aromatic substitution for hydrogen (hereinafter referred to as "NASH") has been disclosed as an alternative method for the prior art method associated with the generation of harmful substances.

One novel process using the NASH is that aniline is directly reacted with nitrobenzene in the presence of tetramethylammonium hydroxide (hereinafter referred to as "TMA(OH)") as a base to prepare 4-NDPA and 4-NODPA (J. Am. Chem. Soc., 1992, 114(23), 9237–8; U.S. Pat. Nos. 5,117,063, 5,252,737, 5,331,099, 5,552,531, 5,633,407). This method has contributed much to significant reducing waste materials, and thus minimizing the generation of harmful substances to the outer environment.

Nevertheless, this method has some recognized disadvantages in that (1) the relatively high-priced TMA(OH) used for the reaction should be re-cycled for economic reasons, (2) aniline is reacted at an ortho-position of nitrobenzene so that 2-nitrodiphenylamine (hereinafter referred to as "2-NDPA") and phenazine are generated as by-products, thus reducing the purity of final product.

There is another novel process using the NASH reaction in which aniline, a starting material, is reacted with azobenzene in the presence of TMA(OH) as a base to prepare 4-ADPA (J. Org. Chem., 1994, 59(19), 5627–5632; U.S. Pat. Nos. 5,382,691, 5,618,979; European Patent No. 726,889; WO No. 95/12569; Japanese Patent No. 9504546). However, this method has proven to be disadvantageous in terms of yield and economic aspects.

SUMMARY OF THE INVENTION

To comply with some problems that the NASH reaction has encountered, an object of this invention is to provide a process for preparing 4-NDPA and 4-NODPA having a higher reactability compared to the reaction between aniline and nitrobenzene only, while significantly reducing the generation of by-products such as phenazine and 2-NDPA.

Another object of this invention is to provide a process for preparing 4-NDPA and 4-NODPA having a higher yield, in a manner such that instead of aniline as a starting material, an anilide compound having an excellent reactability and selectivity is reacted with nitrobenzene, while simultaneously adding aniline to the mixture so as to regenerate some amounts of anilide compound having an excellent reactability.

Another object of this invention is to provide a process for preparing 4-NDPA and 4-NODPA in a higher yield using some general bases such as alkali metals and alkali earth metals, while removing the corrosiveness of reactor can be prevented by blocking the corrosive waste water containing such as chlorine.

To achieve these objectives, this invention aims to use the NASH and is in more detail characterized by the process for preparing 4-NDPA and 4-NODPA, wherein carbanilide is reacted with nitrobenzene in the presence of an appropriate base and solvent, while simultaneously adding aniline to the mixture so as to regenerate a certain amount of carbanilide as a starting material.

DETAILED DESCRIPTION OF THE INVENTION

According to this invention, the process for preparing 4-NDPA and 4-NODPA is schematically expressed by the following scheme.

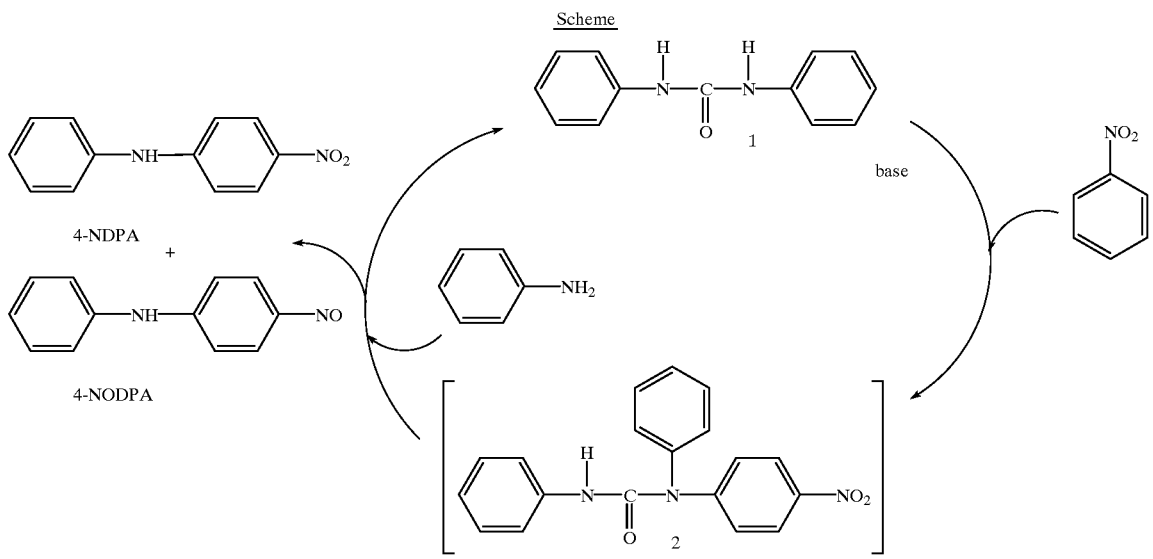

Scheme

According to the recently released paper in line with the direct manufacture of amide compound formed by the NASH reaction, it is reported that benzamide is reacted with nitrobenzene in the presence of TMA(OH) to isolate N-(4-nitrophenyl)benzamide, a relatively stable intermediate, and then methanol and ammonia are added to the mixture and reacted under a pressure reactor to prepare 4-nitroaniline as a final product, while regenerating benzamide (J. Org. Chem., 1993, 58(24), 6883–8; WO No. 93/24447).

As shown in the above scheme of this invention, the compound (2) as an intermediate is not isolated due to its instability. Thus, in line with the regeneration of carbanilide as a starting material, this invention adopts a process of adding a certain amount of the aniline at the initial reaction so as to ensure better yield of final product.

Namely, as noted in the above scheme of this invention, 4-NDPA and 4-NODPA can be easily prepared in a manner such that carbanilide (1) from anilide compounds is selected as a starting material and reacted with nitrobenzene in the presence of aniline and base, while aniline is generated into carbanilide (1) during the process.

More specifically, such process is designed to enhance the yield in the following steps that carbanilide (1) is reacted with nitrobenzene in the presence of base to form an intermediate (2); aniline is added to the mixture to give 4-NDPA and 4-NODPA as a final product, while regenerating carbanilide (1) for re-use in the of reaction. When this process is used, 4-NDPA and 4-NODPA have a higher reactability compared to the reaction between only aniline and nitrobenzene, while significantly reducing the generation of by-products such as phenazine and 2-NDPA.

As mentioned above, 4-NDPA and 4-NODPA are widely used as raw materials of 4-ADPA, an intermediate of antioxidant, via hydrogenation. This invention is advantageous in that carbanilide, while can be easily prepared from urea and aniline, is employed as a starting material and with the addition of sodium hydroxide as a base, 4-NDPA and 4-NODPA can be selectively prepared in a very high yield.

With the addition of aniline, azobenzene is generated as a by-product during the process, but it does not cause any problem, since it can be easily decomposed into aniline under hydrogenation for the manufacture of 4-ADPA and reused via fractional distillation.

In the conventional reaction between aniline and nitrobenzene, the attack of aniline at ortho-position of nitrobenzene results in producing 2-NDPA and phenazine as by-products, thus making it difficult to effectively separate 4-NDPA and 4-NODPA from the reactant. By contrast, when carbanilide is employed as a starting material, any by-products induced by the ortho attack of aniline can be remarkedly reduced the steric hindrance of amide structure.

This invention has several advantages in that (1) 4-NDPA and 4-NODPA can be obtained in a very high yield using the general bases such as alkali metals and alkali earth metals, (2) the corrosiveness of the reactor can be prevented by blocking the corrosive waste water containing such as chlorine, (3) since the yield of the final product is not significantly affected by water and accordingly, any desiccant or distillation device is unnecessary, the production cost can be reduced, and (4) the yield of 4-NDPA and 4-NODPA is further enhanced in such a manner that aniline is added at the initial reaction, while regenerating carbanilide during the process.

According to the manufacturing process of this invention with the aforementioned merits, the solvent used for this invention is independently employed by selecting from the following group of polar organic solvents, or in the form of co-solvent with dimethylsulfoxide in consideration of carbanilide's solubility and blending properties of base: dimethylsulfoxide (hereinafter referred to as "DMSO"), dimethylformamide (hereinafter referred to as "DMF"), N-methyl-2-pyrrolidinone (hereinafter referred to as "NMP"), tetrahydrofuran (hereinafter referred to as "THF"), dioxane, t-buthylalcohol(hereinafter referred to as "t-BuOH"), nitrobenzene and acetonitrile. This invention is not limited to these solvents. It is preferred to use DMSO, DMF and NMP in terms of reactability. In particular, the yield of 4-NDPA is most high in case of DMSO. When the co-solvent is employed, a very high yield of 4-NDPA and 4-NODPA can be obtained in the molar ratio of 1:0–1:5 (DMSO to each of DMF, NMP, dioxane, THF and t-BuOH).

The volumetric ratio of solvent to carbanilide is in the range of 1:100–1:1, preferably in the range of 1:30–1:2.

Meantime, examples of base include inorganic or organic bases which are generally employed. Detailed examples of inorganic base include sodium hydroxide (NaOH), potassium hydroxide(KOH), calcium hydroxide(CA(OH)$_2$), potassium tert-butoxide (t-BuOK), sodium hydride(NaH) and calcium hydride(CaH$_2$). These inorganic bases can be employed together with crown either, a phase transfer catalyst. The examples of organic base include the bases of tetraalkylammonium hydroxides such as a mixture of materials forming TMA(OH) and TMA(OH) but limited to these bases. Among them, it is preferred to select sodium hydroxide, potassium hydroxide and sodium hydride in terms of selectivity or yield of final product. The amount of base employed in the molar ratio of 1–10 times to carbanilide, preferably in the molar ratio of 4–8 times.

According to this invention, carbanilide having an excellent reactability and selectivity is reacted with nitrobenzene in the presence of some appropriate base and solvent as aforementioned. Hence, in an effort to regenerate carbanilide having an excellent reactability and selectivity during the process, aniline is added to the reacting solution.

The amount of aniline is added in the molar ratio of 1–20 to carbanilide, preferably in the molar ratio of 2–10.

With the addition of aniline, azobenzene is generated via self-reaction or reaction with nitrobenzene in the presence of base, but such by-product does not cause any problem, since it can be easily decomposed into aniline for reuse under hydrogenation during the post-process.

It is preferred that the amount of nitrobenzene, so reacted with carbanilide, is in the molar ratio of 0.5–20. If the amount of nitrobenzene is increasing, the reaction rate become faster, and then the reaction yield will be also enhanced within the same time. However, if excess of nitrobenzene is present in the reaction, azoxybenzene is formed as a by-product which results in lowering the selectivity rate of 4-NDPA.

The selectivity of 4-NDPA and 4-NODPA may vary depending on the molar ratio of aniline and nitrobenzene. If more aniline is present than nitrobenzene, the selectivity rate of 4-NODPA is increased, but when the amount of nitrobenzene is more than that of aniline, there is a trend that the selectivity rate of 4-NDPA is increased.

The preferred reaction temperature is in the range of 0–150° C., more preferably in the range of 50–80° C. If the reaction temperature is low, the reaction rate becomes slow, but in case of exceeding 150° C., the yield of 4-NDPA and 4-NODPA becomes poor due to the increasing generation of by-products.

Water of reacting solution, so generated from the initial reaction or during the reaction, can be removed by vacuum distillation or desiccant. The examples of desiccant include potassium carbonate anhydride, sodium sulfate anhydride, magnesium sulfate anhydride, sodium hydroxide, potassium hydroxide, calcium hydride and molecular sieve.

According to this invention, however, any separate process such as the addition of any desiccant or continuous distillation is not necessary due to the fact that the reaction is not greatly affected by the water content, even though the yield of final product can be slightly enhanced via desiccant or continuous distillation.

It is preferred that the reaction is performed under the atmosphere of nitrogen or oxygen. Under the atmosphere of nitrogen, some by-products such as azobenzene and azoxybenzene are generated, while the generation of azoxybenzene is inhibited under the atmosphere of oxygen. However, the reaction atmosphere is not extremely restricted in that azobenzene, generated from aniline, so added, can be easily reused into aniline under hydrogenation during the next process of preparing 4-ADPA.

The reactants and products of this invention were analyzed using a nuclear magnetic resonance (NMR) spectrum and gas chromatography-mass spectrometer (GC-MSD). The quantitative analysis values were determined using the gas chromatography under the following conditions:

Capillary column: ULTRA 2 (crosslinked 5% Ph Me Silicon) 50 m×0.2 mm×0.33 μm).

Carrier gas: nitrogen

Head pressure: 18 psig

Oven: 100° C. (2 min) to 280° C., β=10° C./min

Detector and temperature: FID (280° C.)

Split ratio: 50:1

Make up gas flow-rate: 38 ml

For the quantitative analysis of each product, pyrene was used as an internal standard substance. Also, the factors of gas chromatography on each product were applied to its area rate before analysis so as to calculate the molar ratio (mole %) of each product on the basis of initially added carbanilide.

This invention is explained in more detail based on the following Examples but is not limited by these Examples.

EXAMPLE 1

A mixture of 1.0 g of carbanilide (4.7 mmole), 5.8 g of nitrobenzene (47 mmole), 4.4 g of aniline (47 mmole) and 20 ml DMSO was added to a 100 ml three-necked flask equipped with a cooler and an agitator. Then 1.1 g of sodium hydroxide (28 mmole) was added to the resulting solution 3 times at the interval of 1 hour and reacted under the atmosphere of oxygen at 80° C. for 7 hours.

At the initial reaction, 100 mg of pyrene was added as an internal standard material (this material was also added in all other Examples).

The reacting solution was extracted with ethylacetate, and from the analysis of gas chromatography, 204 mole % of 4-NDPA and 63 mole % of 4-NODPA were obtained as a basis of the initially-added carbanilide.

EXAMPLE 2

The changes in the amounts of 4-NODPA and 4-NDPA, so generated, were observed from this Example, when various amounts of aniline were added.

A mixture of 1.0 g of carbanilide (4.7 mmole), 5.8 g of nitrobenzene (47 mmole), 760 mg of sodium hydroxide (19 mmole) and 5 ml DMSO was added to a 100 ml three-necked flask equipped with a cooler containing 3.2 g of potassium carbonate as a desiccant and an agitator. Then the amounts of aniline were differently added to the mixture and reacted under the atmosphere of oxygen at 80° C. for 5 hours.

After the reacting solution was extracted with ethylacetate, the extract was analyzed on gas chromatography. The results are shown in the following Table 1.

TABLE 1

| Amount of aniline* | Product (mole %) | | |
|---|---|---|---|
| (mole %) | 4-NODPA | 4-NDPA | Azobenze** |
| 2 | 28 | 151 | 8 |
| 5 | 46 | 157 | 6 |
| 10 | 56 | 164 | 4 |

TABLE 1-continued

| Amount of aniline* | Product (mole %) | | |
|---|---|---|---|
| (mole %) | 4-NODPA | 4-NDPA | Azobenze** |

Remarks:
*mole % of aniline to carbanilide, as initially added.
**Molar yield ratio (mole %) on the basis of aniline, as added.

From the above Table 1, it was revealed that azobenzene was generated as a by-product with the addition of aniline. However, the generation of azobenzene is deemed not to be serious in that it can be easily dissolved and reused from a post-process such as hydrogenation designed to prepare 4-ADPA.

Comparative Example 1

The changes in the amounts of 4-NODPA and 43-NDPA, so generated, were observed from this Comparative example using aniline and nitrobenzene only.

The reaction was performed for 5 hours in the same manner as Example 2, except that carbanilide was not employed. After the reacting solution was extracted with ethylacetate, the extract was analyzed on gas chromatography. The results are shown in the following Table 2.

TABLE 2

| Amount of aniline* | Product (mole %) | | |
|---|---|---|---|
| (mole %) | 4-NODPA** | 4-NDPA** | Azobenze*** |
| 2 | — | 7 | 6 |
| 5 | 3 | 12 | 4 |
| 10 | 8 | 30 | 3 |

Remarks:
*Mole % of aniline to carbanilide of Example 2.
**Molar yield ratio (mole %) on the basis of aniline of Example 2.
***Molar yield ratio (mole %) on the basis of aniline, as added.

From the above Table 2, it was revealed that the yield of the final product was significantly reduced, when only aniline was reacted with nitrobenzene without using carbanilide as a starting material.

EXAMPLE 3

The changes in the amounts of 4-NODPA and 4-NDPA, so generated, were observed from this Example, when various amounts of base were added.

A mixture of 1.0 g of carbanilide (4.7 mmole), 5.8 g of nitrobenzene (47 mmole), 4.4 g of aniline (47 mmole) and 5 ml DMSO was added to a 100 ml three-necked flask equipped with a cooler containing 3.2 g of potassium carbonate as a desiccant and an agitator. Then the amounts of sodium hydroxide were differently added to the mixture and reacted under the atmosphere of oxygen at 80° C. for 5 hours.

After the reacting solution was extracted with ethylacetate, the extract was analyzed on gas chromatography. The results are shown in the following Table 3.

TABLE 3

| Amount of aniline* | Product (mole %) | | |
|---|---|---|---|
| (mole %) | 4-NODPA | 4-NDPA | Azobenze** |
| 2 | 15 | 76 | 2 |
| 4 | 56 | 164 | 4 |
| 6 | 96 | 225 | 3 |
| 8 | 106 | 270 | 5 |

Remarks:
*Mole % of sodium hydroxide to carbanilide, as initially added.
**Molar yield ratio (mole %) on the basis of aniline, as added.

From the above Table 3, it was revealed that the yield of product was enhanced in parallel with the increasing amounts of base.

Comparative Example 2

The changes in the amounts of 4-NODPA and 4-NDPA, so generated, were observed from this Comparative example using only aniline and nitrobenzene.

The reaction was performed for 5 hours in the same manner as Example 3, except that carbanilide was not employed. After the reacting solution was extracted with ethylacetate, the extract was analyzed on gas chromatography. The results are shown in the following Table 4.

TABLE 4

| Amount of aniline* | Product (mole %) | | |
|---|---|---|---|
| (mole %) | 4-NODPA** | 4-NDPA** | Azobenze*** |
| 2 | 4 | 16 | 3 |
| 4 | 8 | 30 | 3 |
| 6 | 6 | 25 | 3 |
| 8 | 11 | 46 | 5 |

Remarks:
*Mole % of sodium hydroxide to carbanilide of Example 3.
**Molar yield ratio (mole %) on the basis of aniline of Example 3.
***Molar yield ratio (mole %) on the basis of aniline, as added.

EXAMPLE 4

The changes in the amounts of 4-NODPA and 4-NDPA, so generated, were observed from this Example, when various temperatures were applied.

A mixture of 1.0 g of carbanilide (4.7 mmole), 5.8 g of nitrobenzene (47 mmole), 4.4 g of aniline (47 mmole) and 760 mg of sodium hydroxide (19 mmole) and 5 ml DMSO was added to a 100 ml three-necked flask equipped with a cooler containing 3.2 g of potassium carbonate as a desiccant and an agitator. Then the reaction was performed for 5 hours under various temperature conditions.

After the reacting solution was extracted with ethylacetate, the extract was analyzed on gas chromatography. The results are shown in the following Table 5.

TABLE 5

| | Product(mole %) | | |
|---|---|---|---|
| Temperature (° C.) | 4-NODPA | 4-NDPA | Azobenzene* |
| 100 | 51 | 147 | 3 |
| 80 | 56 | 164 | 4 |
| 50 | 15 | 89 | 1> |

TABLE 5-continued

| | Product(mole %) | | |
|---|---|---|---|
| Temperature (° C.) | 4-NODPA | 4-NDPA | Azobenzene* |

Remarks:
*Molar yield ratio (mole %) on the basis of aniline, as added.

From the above Table 5, it was revealed that when the reaction temperature was low, the reaction rate became slow whereby the yield of the final product was slightly reduced.

EXAMPLE 5

The changes in the amounts of 4-NODPA and 4-NDPA, so generated, were observed from this Example, when various amounts of solvent were added.

A mixture of 1.0 g of carbanilide (4.7 mmole), 5.8 g of nitrobenzene (47 mmole), 4.4 g of aniline (47 mmole) and 1.1 g of sodium hydroxide (28 mmole; added three times at one-hour interval) was added to 5 m DMSO in a 100 ml three-necked flask equipped with a cooler and an agitator, and reacted under the atmosphere of oxygen at 80° C. for 5 hours.

After the reacting solution was extracted with ethylacetate, the extract was analyzed on gas chromatography. The results are shown in the following Table 6.

TABLE 6

| | Product(mole %) | | |
|---|---|---|---|
| DMSO (ml) | 4-NODPA | 4-NDPA | Azobenzene* |
| 20 | 53 | 176 | 8 |
| 10 | 48 | 186 | 4 |
| 5 | 87 | 212 | 3 |

Remarks:
*Molar yield ratio (mole %) on the basis of aniline, as added.

From the above Table 6, it was revealed that the amounts of solvent did not significantly affect the selectivity or yield of final product.

EXAMPLE 6

The changes in the amount of 4- NODPA and 4-NDPA, so generated, were observed from this Example, when various types of base were added.

A mixture of 1.0 g of carbanilide (4.7 mmole), 5.8 g of nitrobenzene (47 mmole), 4.4 g of aniline (47 mmole) and base (28 mmole) was added to 5 ml DMSO in a 100 ml three-necked flask equipped with a cooler and an agitator, and reacted under the atmosphere of oxygen at 80° C. for 3 hours.

After the reacting solution was extracted with ethylacetate, the extract was analyzed on gas chromatography. The results are shown in the following Table 7.

TABLE 7

| | Product(mole %) | | | |
|---|---|---|---|---|
| Base | 4-NODPA | 4-NDPA | Azobenzene* | Phenazine + 2-NDPA* |
| NaOH | 28 | 164 | 3 | 1> |
| KOH | 36 | 133 | 2 | — |
| NaH | 80 | 254 | 6 | 2 |
| t-BuOK | 61 | 182 | 6 | 1 |

Remarks:
*Molar yield ratio (mole %) on the basis of aniline, as added.

From the above Table 7, it was revealed that when sodium hydroxide, potassium hydroxide or sodium hydride as a base was employed, the selectivity or yield of final product was high.

EXAMPLE 7

To determine the role of water, the changes in the amounts of 4-NODPA and 4-NDPA, so generated, were observed from this Example, when water was added to the reacting solution.

A mixture of 1.0 g of carbanilide (4.7 mmole), 5.8 g of nitrobenzene (47 mmole), 4.4 g of aniline (47 mmole) and 752 mg of sodium hydroxide (18.8 mmole) was added to 20 ml DMSO in a 100 ml three-necked flask equipped with a cooler and an agitator. With the addition of water from the outside, the reaction was performed under the atmosphere of oxygen at 80° C. for 3 hours.

After the reacting solution was extracted with ethylacetate, the extract was analyzed on gas chromatography. The results are shown in the following Table 8.

TABLE 8

| Amount of water | Product(mole %) | | |
|---|---|---|---|
| added* | 4-NODPA | 4-NDPA | Azobenzene** |
| 0 | 40 | 135 | 5 |
| 1 | 27 | 134 | 4 |
| 3 | 28 | 109 | 3 |

Remarks:
*Mole % of water to carbanilide, as added.
**Molar yield ratio (mole %) on the basis of aniline, as added.

From the above Table 8, it was revealed that water did not significantly affect the yield of reactants.

EXAMPLE 8

The changes in the amounts of 4-NODPA and 4-NDPA, so generated, were observed from this Example, when various types of solvent were added.

A mixture of 1.0 g of carbanilide (4.7 mmole), 5.8 g of nitrobenzene (47 mmole), 4.4 g of aniline (47 mmole) and 1.6 g of potassium hydroxide (28 mmole) was added to a solvent (10 ml) in a 100 ml three-necked flask equipped with a cooler and an agitator, and reacted at 80° C. for 3 hours in the air.

After the reacting solution was extracted with ethylacetate, the extract was analyzed on gas chromatography. The results are shown in the following Table 9.

TABLE 9

| Solvent Product (mole %) | 4-NODPA | 4-NDPA | 4-ADPA | Azo-benzene* |
|---|---|---|---|---|
| DMSO | 68 | 149 | 2 | 6 |
| NMP | 29 | 89 | — | 5 |
| DMF | — | 14 | — | 1> |
| DMSO:NMP = 1:1 | 93 | 129 | 6 | 6 |
| DMSO:DMF = 1:1 | 12 | 67 | — | 2 |
| DMSO:THF = 1:1 | 60 | 104 | 1> | 4 |
| DMSO:t-BuOH = 1:1 | 94 | 134 | 7 | 7 |
| DMSO:dioxane = 1:1 | 66 | 128 | — | 5 |

Remarks:
*Molar yield ratio (mole %) on the basis of aniline, as added.

From the above Table 9, it was revealed that the most preferred solvent of this invention was DMSO, and the yield of reactants was high using a co-solvent containing DMF, NMP, doxane, THF and t-BuOH with DMSO.

As described above, this invention relates to the process for preparing 4-NDPA and 4-NODPA, wherein an anilide compound as a starting material, which has excellent combinations of properties such as reactability and selectivity, is reacted with nitrobenzene instead of aniline, while adding aniline to the mixture simultaneously and regenerate some amounts of carbanilide with better reactability. The process of this invention is quite effective in preparing 4-aminodiphenylamine, an antioxidant, in an easier manner via post-process with the following merits: (1) higher reactability and better yield can be ensured compared to the reaction between only aniline and nitrobenzene, (2) the generation of b y-products such as phenazine and 2-NDPA can be significantly reduced, and (3) the corrosiveness of reactor can be prevented by blocking the corrosive waste water containing such as chlorine.

What is claimed is:

1. A process for preparing 4-nitrodiphenylamine and 4-nitrosodiphenylamine, wherein carbanilide is reacted with nitrobenzene in the presence of appropriate base and solvent, and then aniline is added to the mixture.

2. The process for preparing 4-nitrodiphenylamine and 4-nitrosodiphenylamine, according to claim 1, wherein said base is employed by selecting from the group consisting of organic bases such as alkali metals, alkali metal hydrides, alkali metal hydroxides and alkali metal alkoxides and organic bases.

3. The process for preparing 4-nitrodiphenylamine and 4-nitrosodiphenylamine, according to claim 2, wherein one or more of said inorganic base is/are employed by selecting from the group consisting of sodium hydroxide, sodium hydride, potassium hydroxide, potassium tert-butoxide, calcium hydroxide and calcium hydride.

4. The process for preparing 4-nitrodiphenylamine and 4-nitrosodiphenylamine, according to claim 2 or 3, wherein said inorganic base is added, together with crown ether, a phase transfer catalyst.

5. The process for preparing 4-nitrodiphenylamine and 4-nitrosodiphenylamine, according to claim 2, tetraalkylammonium hydroxide is employed as said organic base.

6. The process for preparing 4-nitrodiphenylamine and 4-nitrosodiphenylamine, according to claim 1, wherein said solvent is independently employed by selecting from the group consisting of dimethylsulfoxide, dimethylformamide, N-methyl-2-pyrrolidione, nitrobenzene and aniline, or in the form of co-solvent with dimethylsulfoxide.

7. The process for preparing 4-nitrodiphenylamine and 4-nitrosodiphenylamine, according to claim 6, wherein dimethylsulfoxide is independently employed as solvent or in the form of its mixture with such polar solvents with dimethylformamide, N-methyl-2-pyrrolidione, t-butylalcohol, dioxane or tetrahydrofuran.

8. The process for preparing 4-nitrodiphenylamine and 4-nitrosodiphenylamine, according to claim 1, wherein one or more of desiccants is/are employed by selecting from the group consisting of potassium carbonate anhydride, sodium sulfate anhydride, magnesium sulfate anhydride, sodium hydroxide, potassium hydroxide, calcium hydride and molecular sieve.

9. The process for preparing 4-nitrodiphenylamine and 4-nitrosodiphenylamine, according to claim 1, wherein 1–20 times of aniline is employed to the molar ratio of carbanilide.

10. The process for preparing 4-nitrodiphenylamine and 4-nitrosodiphenylamine, according to claim 1, wherein the reaction temperature is in the range of 0–150° C.

11. The process for preparing 4-nitrodiphenylamine and 4-nitrosodiphenylamine, according to claim 1, wherein carbanilide is regenerated, together with the formation of 4-nitrodiphenylamine and 4-nitrosodiphenylamine.

12. The process for preparing 4-nitrodiphenylamine and 4-nitrosodiphenylamine, according to claim 1, wherein the reaction is performed under the atmosphere of nitrogen, oxygen or air.

13. The process for preparing 4-nitrodiphenylamine and 4-nitrosodiphenylamine according to claim 3, wherein said inorganic base is added, together with crown ether, a phase transfer catalyst.

* * * * *

UNITED STATES PATENT AND TRADEMARK OFFICE
CERTIFICATE OF CORRECTION

PATENT NO.    : 6,137,010
DATED         : October 24, 2000
INVENTOR(S)   : Young J. Joo; Jin Eok Kim; Jeong Im Won; Kum Ui Hwang It is certified that error appears in the above-identified patent and that said Letters Patent is hereby corrected as shown below:

Column 6,
Line 62, delete "(mole %)" and insert -- (mole ratio) --;

Column 7,
Line 5, delete "(mole %)" and insert -- (mole ratio) --;
Line 5, delete "Azobenze" and insert -- Azobenzene --;
Line 21, delete "43-NDPA" and insert -- 4-NDPA --;
Line 34, delete "(mole %)" and insert -- (mole ratio) --;
Line 34, delete Azobenze" and insert -- Azobenzene --;
Line 40, delete "%" and insert -- ratio --;
Line 41, delete "aniline" and insert -- carbanilide --;

Column 8,
Line 3, delete "aniline" and insert -- NaOH --;
Line 5, delete "Azobenze" and insert -- Azobenzene --;
Line 11, delete "%" and insert -- ratio --;
Line 31, delete "aniline" and insert -- NaOH --;
Line 32, delete "(mole %)" and insert -- (mole ratio) --;
Line 32, delete "Azobenze" and insert -- Azobenzene --;
Line 38, delete "%" and insert -- ratio --;
Line 39, delete "aniline" and insert -- carbanilide --;

UNITED STATES PATENT AND TRADEMARK OFFICE
CERTIFICATE OF CORRECTION

PATENT NO.   : 6,137,010
DATED        : October 24, 2000
INVENTOR(S)  : Young J. Joo; Jin Eok Kim; Jeong Im Won; Kum Ui Hwang It is certified that error appears in the above-identified patent and that said Letters Patent is hereby corrected as shown below:

Column 10,
Line 46, delete "%" and insert -- ratio --;
Line 46, delete "carbanilide" and insert -- base (NaOH) --;

Column 11,
Line 3, after "Solvent, delete "Product" and insert a tab and isnert -- Product (mole %) --;
Line 4, delete "(mole %)".

Signed and Sealed this

Twenty-fifth Day of December, 2001

Attest:

Attesting Officer

JAMES E. ROGAN
Director of the United States Patent and Trademark Office